US00PP26676P3

(12) United States Plant Patent
Austin

(10) Patent No.: US PP26,676 P3
(45) Date of Patent: May 3, 2016

(54) ***ROSA HYBRIDA* SHRUB NAMED 'AUSTRUSS'**

(50) Latin Name: *Rosa hybrida*
Varietal Denomination: AUStruss

(71) Applicant: David Austin Roses Ltd., Albrighton, Wolverhampton (GB)

(72) Inventor: David J. C. Austin, Wolverhampton (GB)

(73) Assignee: DAVID AUSTIN ROSES LTD., Albrighton, Wolverhampton (GB)

( * ) Notice: Subject to any disclaimer, the term of this patent is extended or adjusted under 35 U.S.C. 154(b) by 152 days.

(21) Appl. No.: 13/999,978

(22) Filed: Apr. 11, 2014

(65) Prior Publication Data

US 2015/0296673 P1 Oct. 15, 2015

(51) Int. Cl.
*A01H 5/00* (2006.01)

(52) U.S. Cl.
USPC ..... Plt./107

(58) Field of Classification Search
USPC ..... Plt./107
See application file for complete search history.

(56) References Cited

PUBLICATIONS

PLUTO Plant Variety Database Oct. 9, 2015. p 1.*

* cited by examiner

*Primary Examiner* — Annette Para
(74) *Attorney, Agent, or Firm* — KPPB LLP

(57) ABSTRACT

A variety of rose plant of the shrub class, named 'AUStruss'. The 'AUStruss' is a variety of rose having medium blooms of a pink blend, which are double, many-petalled and of a deep cup shape, and having a strong fruity fragrance coupled with a long vase life suitable for cut-flower commercial production.

1 Drawing Sheet

Classification: The present invention relates to a new *Rosa hybrida* shrub of the market class 'English Rose'.

Variety denomination: The new plant has the varietal denomination 'AUStruss'.

ORIGIN OF INVENTION

This invention relates to a new and distinct variety of shrub rose plant named 'AUStruss', which was originated from the cross-pollination of the two 'unnamed' and unpatented seedlings of *Rosa hybrida.*

BACKGROUND OF THE INVENTION

The primary objective of this breeding was to produce an English Rose having large blooms of a pink blend, which are double, many-petalled and of a deep cup shape, and having a strong fruity fragrance coupled with a long vase life suitable for cut-flower commercial production.

SUMMARY OF THE INVENTION

Among the features which distinguish the new variety from others presently available and commercial rose cultivars known to the inventor is the following combination of characteristics: large blooms having many petals, a long vase life, a strong fragrance and a pink blend.

Asexual reproduction of the new variety by budding as performed at Bowling Green Lane in Albrighton, Britain shows that the foregoing and other distinguishing characteristics come true to form and are established and transmitted through succeeding asexual propagations. 'AUStruss' may be asexually propagated by budding. The budding successfully occurred on the plant/rootstock *Rosa* 'Inermis' for the observed plants.

COMPARISON WITH PARENTS

The seed and pollen parents of 'AUStruss' are two unnamed seedlings. The new rose may be distinguished from its seed parent, by the following combination of characteristics: the seed parent is a hybrid tea type seedling and purple color compared with the pink blend old-fashioned type English Rose flower of 'AUStruss'. The new rose may be distinguished from its pollen parent, by the following combination of characteristics: the parent is a pink double English Rose type seedling with fewer petals and a lax growth compared with the upright growth of 'AUStruss'.

COMPARISON WITH THE CLOSEST COMMERCIALLY AVAILABLE CULTIVAR

The closest commercially available cultivars to the new variety are the 'AUSboxer' (U.S. Plant Pat. No. 22,947). The new rose may be distinguished from the 'AUSboxer' variety by the following combination of characteristics: the 'AUSboxer' has fewer petals when compared with the 'AUStruss'. In addition, while the petals of both have a pink blend, the blend is different with a red-purple shade being more prevalent in 'AUStruss' while a white shade is more prevalent in 'AUSboxer'. Finally, the buds of 'AUSboxer' are more elongated than those of 'AUStruss'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUStruss' specimens were made at the nursery at David Austin Roses Limited in Albrighton, Wolverhampton, United Kingdom. The following description is of 6 year-old potted rose plants of the new variety, as shown in the attached illustrations. The rose plants, which were observed in the month of June, were grown indoors in a greenhouse in Albrighton, Britain in the month of June. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 2 cm long and 1.7 cm in diameter when the petals start to unfurl. Form: The bud form is broad based. Color: When sepals first divide, the bud color is RHS 60B (red-purple group). When half blown, the upper sides of the petals are RHS 60D (red-purple group) on the margin and RHS 3D (yellow group) in the middle, and the lower sides of the petals are RHS 60D (red-purple group) on the margin and RHS 3D (yellow group) in the middle. Calyx: Shape: star-shaped when the bloom is open, curling back. Length: 8.2 cm. Diameter: 8.2 cm. Sepals: Arrangement: Regular. Color: Upper Surface: RHS 138B (green group). Lower Surface: RHS 143C (green group). Length: 3.5 cm. Width: between 9-12 mm. Shape: Lanceolate. Surface texture: Upper Surface: Hirsute. Lower Surface: Glandular. Number: There are 3 lightly appendaged sepals, and 2 unappendaged sepals with hairy edges. Receptacles: Color: RHS 144A (yellow-green group). Shape: funnel. Size: medium, about 1 cm high×1.1 cm wide. Surface: Smooth. Peduncle: Length: medium, averaging about 8 cm. Surface: Glandular. Color: RHS 144A (yellow-green group). Strength: Strong.

*Blooms.*—Size: Large, average open diameter is about 9 cm. Borne: Several together. (Note: the inflorescence when the shrub is growing naturally may hold between 4 and 6 blooms, and then has a rounded shape. When grown commercially for cut-flower production the stems are disbudded to ensure the blooms are grown singly.) Stems: Strength: Strong, average length is about 60 cm. Diameter: 6 mm. Form: When first open, bloom is cupped. Permanence of bloom: flattens.

*Petalage.*—Number of petals under normal conditions: 140. Color: The upper sides of the petals are RHS 65B (red-purple group) and RHS N155C (white group). The reverse sides of the petals are RHS 75D (purple group) and RHS 65B (red-purple group). The base of the petals has a yellow spot (RHS 3D, yellow group) on the inner side, and RHS 4D (yellow group) on the outer side. Variegations: Pink blend. Discoloration: The general tonality at the end of the first day is RHS 65B (red-purple group), and at the end of the third day is RHS 75D (purple group). With further aging the color then further changes to RHS N155C (white group). Fragrance: Strong. Character of fragrance: fruity.

*Petals.*—Texture: Satiny. Size: Variable: From petals taken from the same 3$^{rd}$ whorl, the size varies between: Width: 15-50 mm. Length: 20-53 mm. Surface: Smooth. Shape: Obovate. (Note: the shape is mainly obovate, but inside the 3$^{rd}$ outer whorl of petals, many petals are folded to varying degrees.) Margin: Cuspidate tips with little reflexing of the margin. Apex Shape: Rounded, with cuspidate tips. Base Shape: Acute. Form: Incurved. Arrangement: Rosette formation. Petaloids: Number: about 5. Color: RHS 6D (yellow group). Length: 6 mm. Width: 3 mm. Shape: Oval. Margin: Entire. Persistence: Petals drop off cleanly before drying. Lastingness: On the plant: not tested. As a cut flower: About 10 days.

*Reproductive parts.*—Stamens: Number: 6-10. Length: 5 mm. Anthers: Length: 2.5 mm. Color: RHS 14C (yellow-orange group). Arrangement: Mixed with petaloids. Filaments: Color: RHS 4A (yellow group). Length: 3 mm. Pollen: Color: RHS 23A (yellow-orange group). Pistils: Number: 40. Length: 14.5 mm. Styles: Color: RHS 158D (yellow-white group). Length: 14 mm. Stigmas: Color: RHS 3B (yellow group). Length: 0.5 mm. Hips: None Observed.

Plant characteristics:

*Plant form.*—Shrub, English Rose.

*Plant growth.*—Medium.

*Age to maturity.*—Two years.

*Mature plant.*—Height: 92 cm. Width: 75 cm.

*Rootstock.*—*Rosa* 'Inermis' for the observed plants.

*Foliage.*—Number: Leaflets on normal mid-stem leaves is: mostly 5 and sometimes 7. Size: Medium, about 15 cm long×11 cm wide. Quantity: Abundant. Number of leaves per flowering stem is: 11. Color: New foliage: Upper side: RHS 144A (yellow-green group) tinged with RHS 60A (red-purple group) at the very edges. Lower side: RHS 144A (yellow-green group). Old foliage: Upper side: RHS 147A (yellow-green group). Lower side: RHS 138A (green group).

*Leaflets.*—Size: About 6.5 cm long×4 cm wide. Shape: Pointed oval. Base Shape: Rounded. Apex Shape: Acuminate. Texture: Leathery. Edge: Serrated. Serrations: Single. Petiole: Color: RHS 137A (green group). Length: 4 cm. Width: 2 mm. Surface Texture: Prickly. Petiole Rachis: Color: RHS 143C (green group) on underside and RHS 137C (green group) on upperside. Underside: with prickles. Stipules: Length: 2.9 cm, glandular. Color: RHS 143C (green group). Auricle: Shape: Lanceolate. Length: 5 mm. Width: 2 mm. Color: RHS 143A (green group). Vein Color: Same as leaf color. Venation Pattern: Reticulate.

*Wood.*—New Wood: Color: RHS 181B (greyed-red group). Bark: Smooth. Old Wood: Color: RHS 144A (yellow-green group). Bark: Smooth.

*Branching habit.*—Number: None.

*Stems.*—Mature Stem: Length: 76 cm. Diameter: 8 mm. Internode Distance: 3-5 cm. The above measurements are all variable, depending on growing conditions in a season. Stem Pubescence Present: No.

*Prickles.*—Quantity: On main canes from base: Ordinary. Number per stem length: 14 per 30 cm. Form: Deep concave. Length: 9 mm. Color when young: RHS 181B (greyed-red group). Color when mature: RHS 160A (greyed-yellow group).

*Small prickles.*—Quantity: Main stalk: None Laterals: None.

*Disease resistance.*—Mildew: Resistant. Blackspot: Not tested. Rust: Not tested.

*Pest resistance.*—Not tested.

*Winter hardiness.*—Not tested.

*Growing conditions.*—Normal greenhouse conditions.

What is claimed is:

1. A new and distinct variety of rose plant of the shrub class suitable for cut flower production, substantially as herein shown and described.

* * * * *

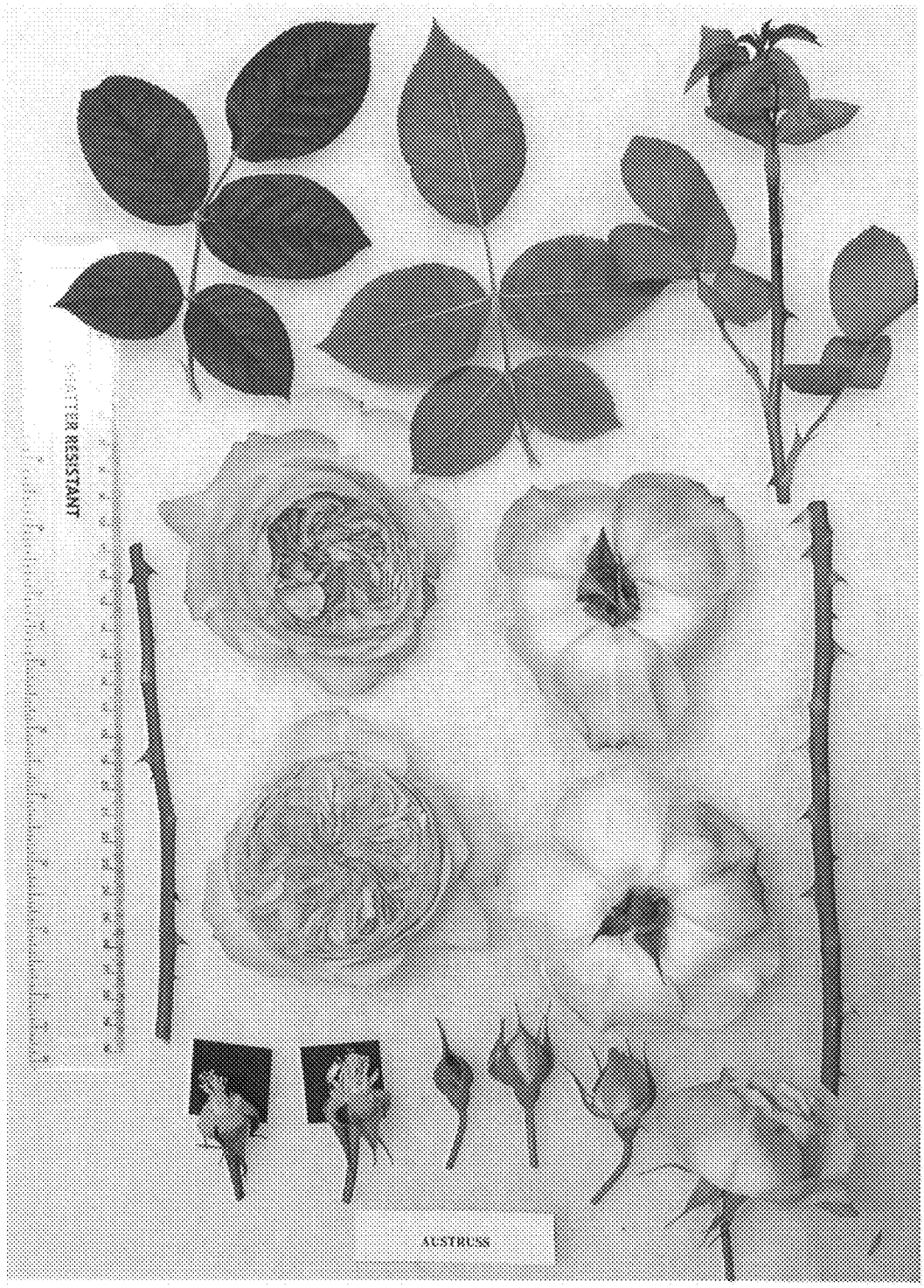
AUSTRUSS
SOME THE RESISTANT